United States Patent [19]
Fukumoto et al.

[11] Patent Number: 5,603,927
[45] Date of Patent: Feb. 18, 1997

[54] MATERIAL FOR REMOVING OFFENSIVE ODOR

[75] Inventors: Kazuhiro Fukumoto; Seiji Onoda; Masahiro Sugiura; Mitsumasa Horii; Hiroaki Hayashi, all of Aichi, Japan

[73] Assignee: Kabushiki Kaisha Toyota Chuo Kenkyusho, Aichi-ken, Japan

[21] Appl. No.: 162,891

[22] Filed: Dec. 8, 1993

[30] Foreign Application Priority Data

Dec. 8, 1992 [JP] Japan .................... 4-352080

[51] Int. Cl.$^6$ ...................... A61L 9/01; A61L 2/16
[52] U.S. Cl. ........................ 424/76.1; 424/400
[58] Field of Search .................. 424/76.1, 400; 564/90, 220, 305; 252/190, 184

[56] References Cited

U.S. PATENT DOCUMENTS 4,443,354  4/1984  Eian et al. .................... 502/62
5,098,700  3/1992  Nakai et al. ................. 424/76.1
5,135,740  8/1992  Katz et al. .................. 424/76.1
5,231,063  7/1993  Fukumoto et al. ............ 424/76.1

OTHER PUBLICATIONS

Japanese Laid-Open Patent Publication No. 23588(1993).

*Primary Examiner*—Thurman K. Page
*Assistant Examiner*—Raj Bawa
*Attorney, Agent, or Firm*—Oblon, Spivak, McClelland, Maier & Neustadt, P.C.

[57] ABSTRACT

A material for removing offensive odors, which efficiently removes offensive odors, especially aldehydes, without being influenced by the ambient atmosphere such as humidity. It contains at least one acid salt selected from the group consisting of acid salts of aniline halides, acid salts of esters of aminobenzoic acid, acid salts of sulfanilamide or its derivatives, acid salts of aminoacetanilide and acid salts of aminoacetophenone. It may be supported on a porous carrier. The removing capacity of the material is not lowered by the variation of the ambient atmosphere of humidity and temperature. The material efficiently removes aldehydes.

18 Claims, 3 Drawing Sheets

MATERIAL FOR REMOVING OFFENSIVE ODOR

BACKGROUND OF THE INVENTION

1. Field of the Invention

The present invention relates to a material for removing offensive odors such as, for example, a deodorizer effective in removing offensive odors of ammonia, hydrogen sulfide, acetaldehyde, etc. originating from industrial and automotive exhaust gasses, and other smells of tobacco, human body, human waste, foods in refrigerators, etc. encountered in daily life, or an adsorbent for treating such gaseous substances, etc.

2. Description of the Related Art

Offensive odors from human activities in automobiles, kitchens, living rooms, offices, etc. include various mixed offensive odors. For instance, it is said that offensive odors in a car contain thousands of components originating from cigarette smoke, sweat, exhaust gas, dust, etc. The Offensive Odor Control Law (Japanese law) describes the following twelve malodorous components as especially important, namely, ammonia, methyl mercaptan, hydrogen sulfide, methylsulfide, methyl disulfide, trimethylamine, acetaldehyde, styrene, propionic acid, n-butyric acid, n-valeric acid, and iso-valeric acid.

The conventional methods of removing such offensive odors are by masking with an aromatic or by adsorption with activated carbon, silica gel, etc.

However, these methods have disadvantages. Masking with an aromatic does not remove the components of offensive odors in itself, and there may be an instance where the aromatic itself smells unpleasant. As to the physical adsorption by the adsorbents such as activated carbon, silica gel, etc., the kinds of malodorous components are limited depending on adsorbents to be used. For example, activated carbon is not effective at all for odors originating from such basic substances as ammonia, trimethylamine, etc.

To overcome the drawbacks, a chemical removing method has been proposed. It removes offensive odors by chemical neutralization. It permits the removal of both acid odors of acetaldehyde, hydrogen sulfide, etc. and basic odors of ammonia, trimethylamine, etc. More precisely, acid odors and basic odors are removed by neutralization with a basic adsorbent and an acid adsorbent, respectively.

However, such chemical adsorbents have also a disadvantage that the basic adsorbent and the acid adsorbent react with each other and become deactivated because of their properties, when they are supported on the same carrier or dispersed in the same liquid simultaneously.

Under the situation, the present inventors found a composite adsorbent which adsorbs and removes both acid odors and basic odors and which comprises an acid salt of an aromatic amino acid, an acid, and a transition metal compound, iodine or an iodine compound as active ingredients (Japanese Patent Application Laid-Open Nos. 3-296434 and 5-23588).

Of components of offensive odors, aldehydes such as acetaldehyde, etc. are the most evil-smelling. In particular, it has become important to remove aldehydes from high-humidity places such as living rooms and cars in the rainy season or in rainy days.

The above-mentioned composite adsorbent developed by the present inventors may adsorb and remove both acid odors and basic odors, but it has been found that the adsorbent is still unsatisfactory for adsorbing and removing aldehydes under the above-mentioned high-humidity condition.

SUMMARY OF THE INVENTION

The present invention has been made in consideration of the above-mentioned problems in the related art, and its object is to provide a material for removing offensive odors, which may efficiently remove offensive odors, especially aldehydes, without being influenced by the ambient atmosphere such as humidity, etc.

The material for removing offensive odors of the present invention is characterized by containing at least one acid salt selected from the group consisting of acid salts of aniline halides, acid salts of esters of aminobenzoic acid, acid salts of sulfanilamide or its derivatives, acid salts of aminoacetanilide and acid salts of aminoacetophenone.

The material for removing offensive odors of the present invention may remove offensive odors from gases such as exhaust gas, etc., even though the ambient atmosphere including humidity, temperature, etc. varies. In particular, it efficiently removes aldehydes therefrom.

These and other objects, constitutions and effects of the present invention will be explained in detail by preferred embodiments with reference to the attached drawings.

DETAILED DESCRIPTION OF THE INVENTION

Figure 1:
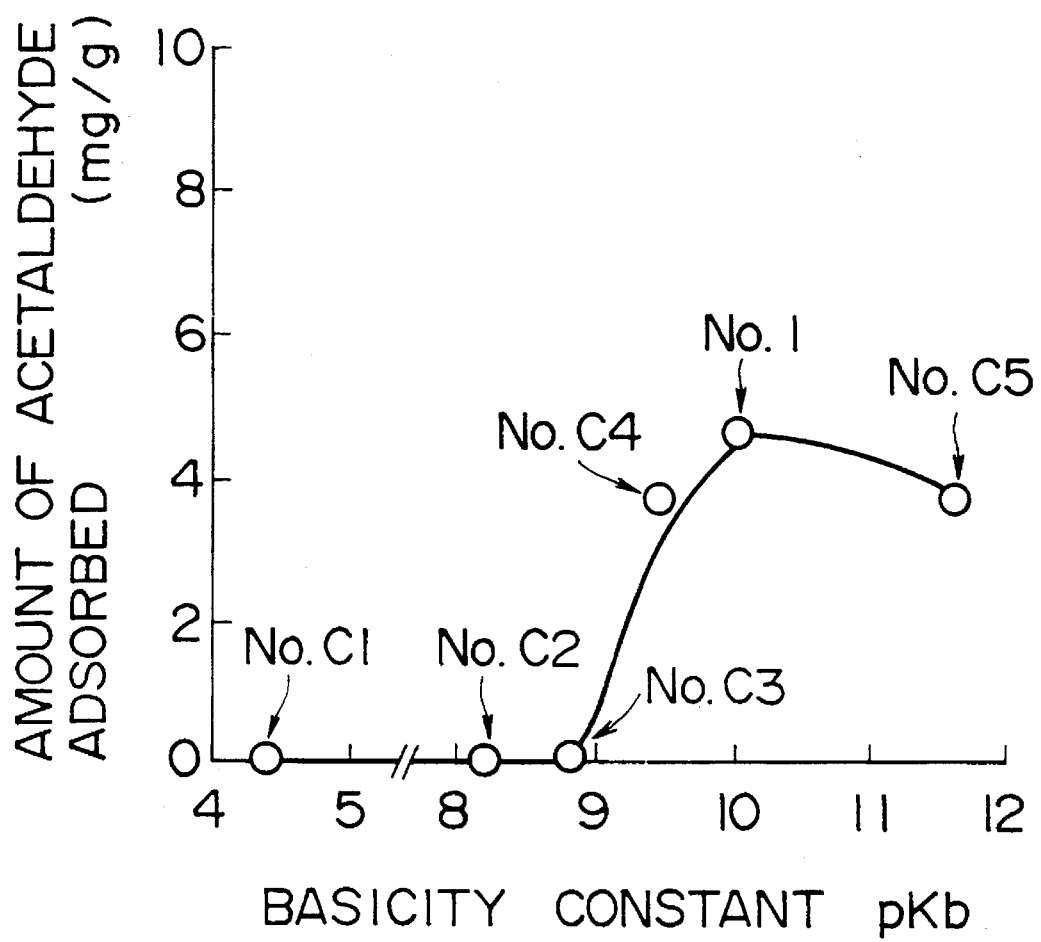
FIG. 1 is a diagram showing the acetaldehyde-adsorbing capacities of the removing material samples prepared in the example and the comparative example which follow hereunder.

The material for removing offensive odors of the present invention contains at least one acid salt selected from the group consisting of acid salts of aniline halides, acid salts of esters of aminobenzoic acid, acid salts of sulfanilamide or its derivatives, acid salts of aminoacetanilide and acid salts of aminoacetophenone.

Since the material for removing offensive odors of the present invention contains at least one selected from acid salts of aniline halides, acid salts of esters of aminobenzoic acid, acid salts of sulfanilamide or its derivatives, acid salts of aminoacetanilide and acid salts of aminoacetophenone, it may still remove offensive odors from gases such as exhaust gas, etc., even though the ambient atmosphere including humidity, temperature, etc. varies. In particular, it efficiently removes aldehydes therefrom. Though not clear, the reasons may be presumed as follows:

It is presumed that one of reactions between the removing material of the present invention and an aldehyde will be a nucleophilic addition reaction to the partial positively-charged carbon of the carbonyl group (C=O) by the lone pair of electrons on the nitrogen atom. Precisely, the removing material of the present invention releases $H^+$ (proton) from the acid which forms the acid salt or from the acid partly freed from the acid salt, and the proton is added to the carbonyl group (C=O) in the aldehyde structure to increase the positive chargeability of the carbonyl carbon, thereby yielding the effect for accelerating the nucleophilic addition reaction.

The ionization of the amino group ($NH_3^+$) in the removing material causes localization of the electrons therein, with the result that the ring is activated to also accelerate the ring substitution reaction. It is also considered that these effects are synergistic. Hence, it is believed that the removing material of the present invention will chemically decompose and remove offensive odors such as aldehydes, etc.

The excellent property of the removing material of the present invention stems from the acid salts of substances having a suitable basicity in order to accelerate the above-mentioned reactions. Precisely, the electron attracting substituents of halogens (in aniline halides), sulfonic acid amides (in sulfanilamide or its derivatives), acetamide group (in aminoacetanilide) and carbonyl group (in esters of aminobenzoic acid and aminoacetophenone) lower the basicity of the amines, with the result that the bonding force of the amines to acids is weakened. Therefore, the reactivity of the removing material with offensive odors is increased so that its performance of removing offensive odors is improved.

Aniline halides are substances that will be represented by the following molecular formula (1), where X is a halogen such as fluorine, iodine, chlorine, bromine, etc., and the substituent may be positioned in the benzene ring at any of o-, m- and p-positions.

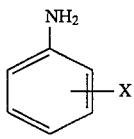
(1)

Esters of aminobenzoic acid are substances that will be represented by the following molecular formula (2), where R is an alkyl group, and the substituent may be positioned in the benzene ring at any of o-, m- and p-positions.

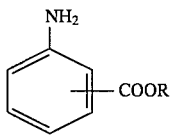
(2)

Sulfanilamide and its derivatives are substances that will be represented by the following molecular formula (3), where R is hydrogen, a substituent having homocyclic ring(s) or a substituent having heterocyclic ring(s), and the substituent may be positioned in the benzene ring at any of o-, m- and p-positions.

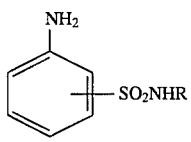
(3)

Aminoacetanilide is a substance that will be represented by the following molecular formula (4), where the substituent may be positioned in the benzene ring at any of o-, m- and p-positions.

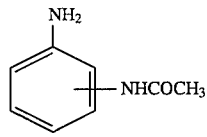
(4)

Aminoacetophenone is a substance that will be represented by the following molecular formula (5), where the substituent may be positioned in the benzene ring at any of o-, m- and p-positions.

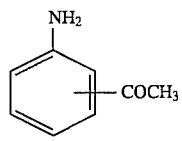
(5)

The acid salts of the above-mentioned substances may be those as they are. Alternatively, the acid salts may also be prepared from the above-mentioned substances by adding acids thereto so as to ammonium-ionize the amino group of the substances to give their acid salts.

The above-mentioned aniline halides, esters of aminobenzoic acid, sulfanilamide or its derivatives, aminoacetanilide and aminoacetophenone do not have a carboxyl group which easily undergoes molecular association, unlike aromatic amino acids. If they undergo molecular association, their reactivity on aldehydes will be lowered with the result that they could not have a sufficient property as a material for removing aldehyde.

Of the above-mentioned substances, those having a basicity constant pKb of 9.4 or more (desirably about 10) are preferred.

The acid for forming the acid salts includes inorganic acids such as hydrochloric acid, nitric acid, sulfuric acid, phosphoric acid, etc., and organic acids such as citric acid, malonic acid, malic acid, oxalic acid, etc.

There are no restrictions on the usage of the material for removing offensive odors of the present invention. The acid salts of the above-mentioned substances may be used as such in powder form or in the form of solution in an adequate concentration. For a better effect, however, it is preferred that the acid salts of the above-mentioned substances are used in the form of dispersion supported on a porous carrier.

Examples of the porous carrier include inorganic porous carriers such as sepiolite, palygorskite, activated carbon, zeolite, activated carbon fiber, activated alumina, sepiolite-mixed paper, silica gel, activated clay, vermiculite, diatomaceous earth, etc., and organic porous carriers such as pulp, fibers, cloth, polymeric porous body, etc. Preferred are sepiolite, palygorskite, activated carbon, activated alumina, and zeolite. The carrier may be freely selected, depending upon the kind of the offensive odors to be adsorbed.

The porous carrier supports the acid salts of the above-mentioned substances as the active ingredients in its pores uniformly, so that the active ingredients have an enlarged area that comes into contact with the gasses containing offensive odors and hence adsorb them efficiently. In addition, the porous carrier itself has the capability for adsorption and hence enhances the performance of the removing material. For example, activated carbon and sepiolite are effective, respectively, in adsorption of offensive odors originating from hydrocarbon and lower fatty acids.

The porous carrier may be in the form of sheet, honeycomb, powder, pellet, granule, plate, fiber, etc.

There are no restrictions on the amounts of the acid salts of the above-mentioned substances to be supported on the porous carrier. However, it is preferred that the amounts are within the range of from 0.1 to 30 parts by weight, relative to 100 parts by weight of the carrier. Within the range, the effect of the material for removing offensive odors is extremely high. More preferably, the amounts are within the range of from 0.5 to 15 parts by weight, relative to 100 parts by weight of the carrier.

The material for removing offensive odors of the present invention may contain other components effective in removing offensive odors, in addition to the acid salts of the above-mentioned substances. For instance, it may additionally contain other adsorbing components, for example, acid salts of aromatic amino acids, acids, transition metal compounds (e.g., copper chlorides, etc.), iodine or iodides, etc., such as those described in Japanese Patent Application Laid-Open Nos. 3-296434 and 5-23588, to be a composite material capable of simultaneously removing various offensive odors. In particular, the combination comprising the acid salts of the above-mentioned substances of the present invention, acids and iodine or iodides may be an excellent composite material. In the composite material, the acid salts of the above-mentioned substances of the present invention remove aldehydes, while acids remove basic odors and iodine or iodides remove sulfides. Thus, the composite material may remove a composite odor consisting of various offensive odors. For preparing the composite material, excess amounts of acids may be added to the above-mentioned substances when preparing the acid salts of the above-mentioned substances of the present invention, i.e. when adding acids to the above-mentioned substances, whereby a mixture comprising the acid salts of the above-mentioned substances and the residual acids may be obtained.

The acid in the above-mentioned composite material includes inorganic acids such as hydrochloric acid, nitric acid, sulfuric acid, phosphoric acid, etc., and organic acids such as citric acid, malonic acid, malic acid, oxalic acid, etc. The iodide in the same includes ammonium iodide, sodium iodide, potassium iodide, etc. The transition metal compound in the same includes chlorides, bromides, fluorides, etc. of copper, zinc, cobalt, nickel, etc.

For supporting the above-mentioned active ingredients in the above-mentioned composite material on the porous carrier, the amounts of the active ingredients are preferably within the range of from 0.1 to 30 parts by weight, relative to 100 parts by weight of the carrier. More preferably, they are within the range of from 0.5 to 15 parts by weight, relative to 100 parts by weight of the carrier.

Next, the method of preparing the material for removing offensive odors of the present invention will be explained below.

There are no restrictions on the method by which the material for removing offensive odors of the present invention is supported on a porous carrier. Preferably, however, the acid salts of the above-mentioned substances are finely ground, and the resulting powder is mixed with a fine powder of a porous carrier and shaped so that the former is supported by the latter. More preferably, the acid salts are dissolved in water or any other soluble solvent, and the resulting solution is infiltrated into a porous carrier so that the salts are supported by the carrier. The latter method is effective for the uniform dispersion of the acid salts of the above-mentioned substances on the porous carrier, which leads to the maximum removing performance.

Since the material for removing offensive odors of the present invention is especially effective in removing aldehydes, as mentioned above, it may be used as a material for removing various offensive odors originating from human activities in automobiles, kitchens, living rooms, offices, toilets, etc. and also as an adsorbent or the like for treating gasses containing such offensive odors.

Examples of the present invention will be explained hereunder.

7.8 g of an impregnant comprising an acid salt of the substance shown in Table 1 was uniformly sprayed over an activated carbon fiber sheet (weight: 4.6 g), and the sheet was then dried under heat at about 100° C. for one hour. Thus, removing material samples were prepared (Sample Nos. 1 to 5 in Table 1).

For comparison, comparative removing material samples (Sample Nos. C1 to C5 in Table 1) were prepared in the same manner as above, except that an acid salt of glycine as an acid salt of an aliphatic amino acid; an acid salt of aniline, an acid salt of p-aminophenol or an acid salt of p-anisidine as an acid salt of an aromatic amine having no electron attracting substituent; and an acid salt of p-aminobenzoic acid as an acid salt of an aromatic amino acid were used as active ingredients.

The compositions of the impregnant used herein are shown in Table 1.

TABLE 1

| Sample No. | Composition of Liquid Additive (weight, g) |
| --- | --- |
| Examples | |
| 1 | P-chloroaniline (3.14) + Aqueous solution of 85% phosphoric acid (5.673) + Water (200) |
| 2 | Ethyl p-aminobenzoate (3.14) + Aqueous solution of 85% phosphoric acid (4.380) + Water (200) |
| 3 | Sulfanilamide (3.14) + Aqueous solution of 85% phosphoric acid (4.204) + Water (200) |
| 4 | P-aminoacetanilide (3.14) + Aqueous solution of 85% phosphoric acid (4.821) + Water (200) |
| 5 | P-aminoacetophenone (3.14) + Aqueous solution of 85% phosphoric acid (5.357) + Water (200) |
| Comparative Examples | |
| C1 | Glycine (3.14) + Aqueous solution of 85% phosphoric acid (4.827) + Water (200) |
| C2 | P-aminophenol (3.14) + Aqueous solution of 85% phosphoric acid (6.641) + Water (200) |
| C3 | P-anisidine (3.14) + Aqueous solution of 85% phosphoric acid (5.880) + Water (200) |
| C4 | Aniline (3.14) + Aqueous solution of 85% phosphoric acid (3.893) + Water (200) |
| C5 | P-aminobenzoic acid (3.14) + Aqueous solution of 85% phosphoric acid (5.280) + Water (200) |

The thus obtained removing material samples were tested for their adsorbability in the following manner.

0.5 g of each of the removing material samples (Sample No. 1 and Sample Nos. C1 to C5) was placed in a gas-impermeable bag. Next, an aqueous solution of acetaldehyde was heated and vaporized, and 5 liters of a mixture comprising the vapor and a humidity-conditioned air (25° C., RH) was introduced into the bag. The concentration of the acetaldehyde vapor in the mixture to be introduced into the bag was varied by varying the amount of the aqueous acetaldehyde solution to be vaporized. Thus, four bags for one sample, each having a different acetaldehyde vapor concentration, were prepared. The bags were left to stand statically in a thermostat having a temperature of 25° C. After about 24 hours, the concentration of the gas that had remained in the bag was measured by gas chromatography, and it was translated into the amount of adsorption according to the formula (6) below. On the basis of the amount thus obtained, the adsorption isotherm was formed for each sample. By interpolating the adsorption isotherm, the amount of acetaldehyde adsorbed by the sample being put in the bag having an acetaldehyde concentration of 3 ppm was obtained, whereby the adsorbability of the sample was evaluated. The results are shown in FIG. 1.

$$q = \frac{Mw \times V \times 273 \times (C_b - C_s)}{22.4 \times (273 + t) \times 10^3 \times w} \qquad (6)$$

where q: amount of adsorption (mg/g)

Mw: molecular weight of malodorous substance

V: capacity of bag (liter)

$C_b$: concentration of malodorous substance in bag not containing the sample (ppm)

$C_S$: concentration of malodorous substance in bag containing the sample (ppm)

t: test temperature (°C.)

w: weight of sample (g)

It is obvious from FIG. 1 that the removing material sample of the present invention (Sample No. 1) is superior in the capacity of removing acetaldehyde to the comparative removing material samples (Sample Nos. C1 to C5) and especially that p-chloroaniline having a basicity constant pKb of 10.01 has the maximum capacity.

The basicity constant pKb in FIG. 1 is defined by the following formula (7):

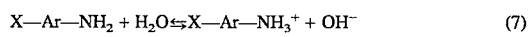

$$Kb = \frac{[X-Ar-NH_3^+][OH^-]}{[X-Ar-NH_2]}$$

$pKb = -\log Kb$ where

X: OH, $OCH_3$, H, Cl or COOH

Ar: arylene group or methylene group

Next, the removing material samples were tested for the variation in the adsorbing capacity, varying the humidity and the temperature in the ambient atmosphere.

Figure 2:
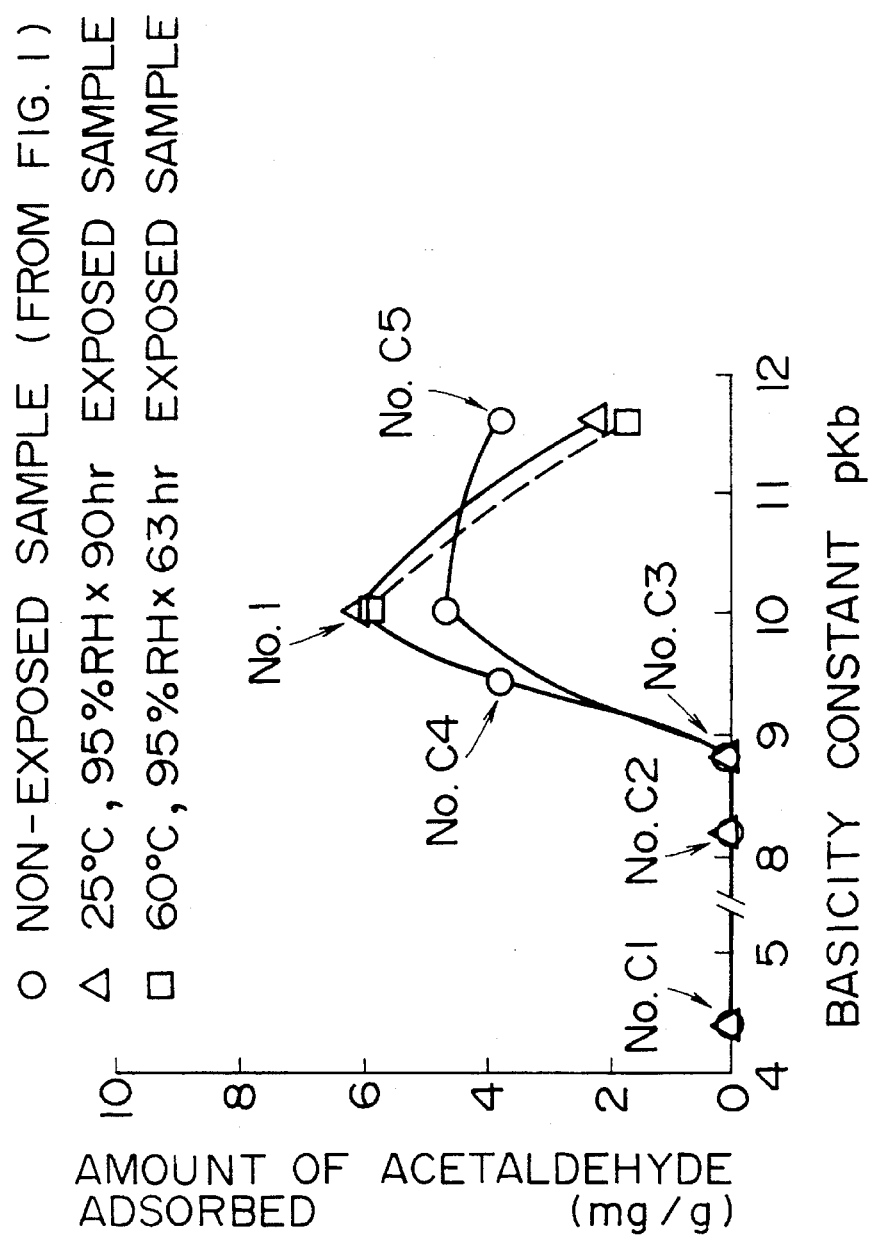
FIG. 2 is a diagram showing the acetaldehyde-adsorbing capacities of the removing material samples prepared in the example and the comparative example.

The removing material samples (Sample No. 1 and Sample Nos. C1 to C5) were exposed to air at 25° C. and 95% RH for 90 hours or to air at 60° C. and 95% RH for 63 hours, and they were tested for the acetaldehyde-adsorbing capacity by the same method (for adsorption test) as above. The adsorption test was conducted at a temperature of 25° C. and a humidity of 60% RH. The results obtained are shown in FIG. 2. FIG. 2 also has the data of the non-exposed samples (of FIG. 1).

It is obvious from FIG. 2 that the removing material sample of the present invention (Sample No. 1) is still superior to the comparative removing material samples (Sample Nos. C1 to C5) and is not deteriorated in adsorbability even though the ambient atmosphere of humidity and temperature varies.

In addition, the removing material samples of the present invention were tested for the adsorbing capacity in the following manner.

0.5 g of each of the removing material samples (Sample Nos. 1 to 5) was placed in a gas-impermeable bag. Next, a pre-determined amount of an aqueous solution of acetaldehyde was heated and vaporized to have an acetaldehyde concentration in air of about 1000 ppm. 5 liters of the mixture of the acetaldehyde vapor and a humidity-conditioned air (25° C., 60% RH) was introduced into the bag. The bag was left to stand statically in a thermostat having a temperature of 25° C, whereupon the concentration of acetaldehyde in the bag was measured by gas chromatography at determined time intervals. The results are shown in FIG. 3.

Figure 3:
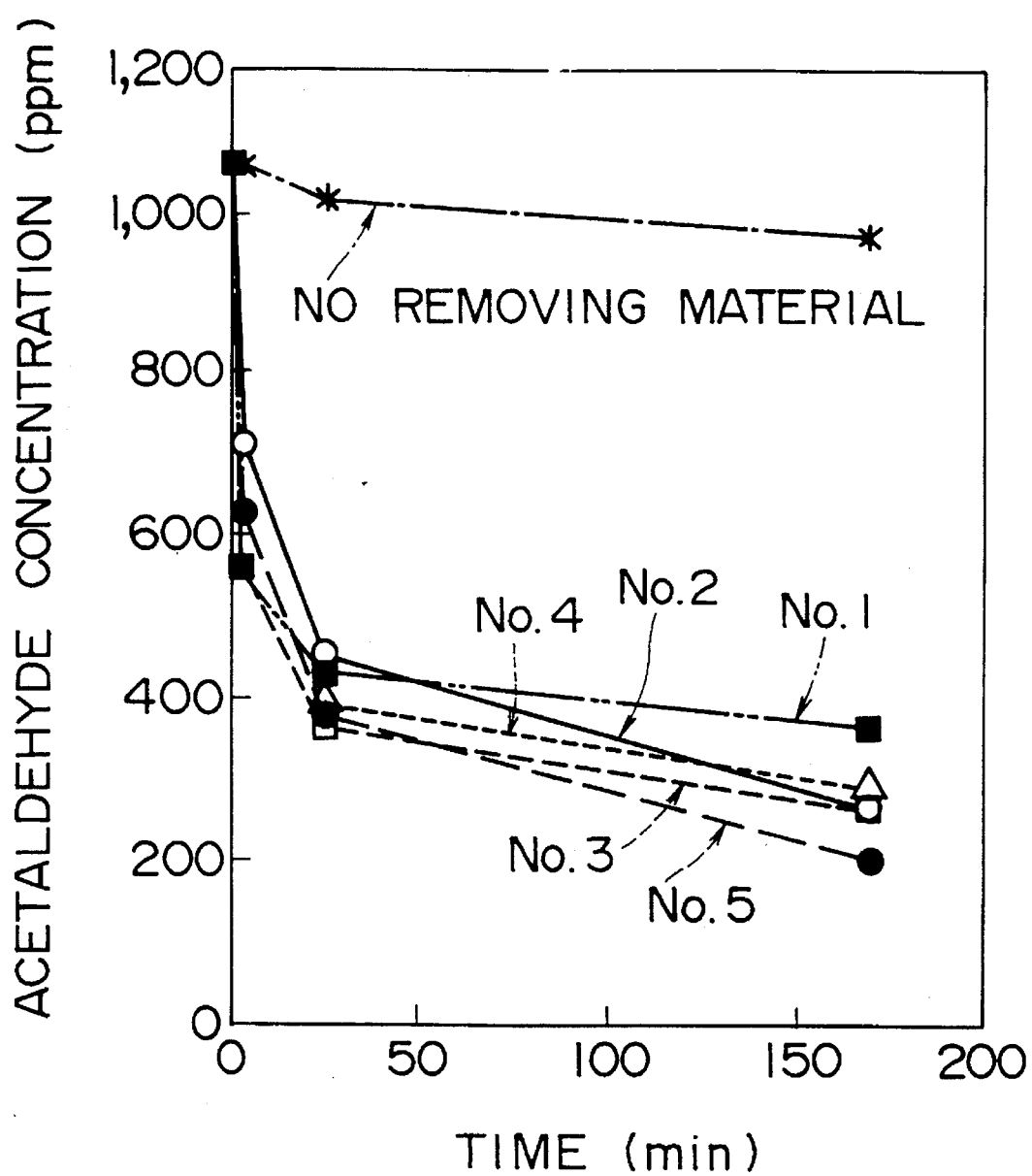
FIG. 3 is a diagram showing the acetaldehyde-adsorbing capacities of the removing material samples prepared in the example.

It is obvious from FIG. 3 that the removing material samples of the present invention (Sample Nos. 1 to 5) have an excellent acetaldehyde-removing capacity.

What is claimed is:

1. An active compound supported by an inert solid porous carrier for removing offensive odors from an acetaldehyde-containing gas, consisting essentially of at least one acid salt of an aminobenzene compound having the formula:

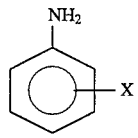

wherein X is halogen; —COOR, wherein R is an alkyl group; —$SO_2NHR$, wherein R is hydrogen; —NH-$COCH_3$ or $COCH_3$.

2. The active compound of claim 1, which has a basicity constant pKb of 9.4 or more.

3. The active compound of claim 1, wherein said acid salt is a salt of an inorganic acid selected from the group consisting of hydrochloric acid, nitric acid, sulfuric acid and phosphoric acid.

4. The active compound of claim 1, wherein said acid salt is a salt of organic acid selected from the group consisting of citric acid, malonic acid, malic acid and oxalic acid.

5. The active compound of claim 1, wherein said inert solid porous carrier is an inorganic porous carrier selected from the group consisting of sepiolite, palygorskite, activated carbon, zeolite, activated alumina, sepiolilte-mixed paper, silica gel, activated clay, vermiculite, and diatomaceous earth.

6. The active compound of claim 1, wherein said inert solid porous carrier is an organic porous carrier selected from the group consisting of pulp, fibers, cloth, and polymeric porous bodies.

7. The active compound of claim 1, wherein said at least one acid salt of an aminobenzene compound is an acid salt of an aniline halide.

8. The active compound of claim 1, wherein said at least one acid salt of an aminobenzene compound is an acid salt of an ester of aminobenzoic acid.

9. The active compound of claim 1, wherein said at least one acid salt of an aminobenzene compound is an acid salt of sulfanilamide.

10. The active compound of claim 1, wherein said at least one acid salt of an aminobenzene compound is an acid salt of aminoacetanilide.

11. The active compound of claim 1, wherein said at least one acid salt of an aminobenzene compound is an acid salt of aminoacetophenone.

12. The active compound of claim 1, wherein said at least one acid salt of said aminobenzene compound is supported on said porous carrier in an amount of from 0.1 to 30 parts by weight relative to 100 parts by weight of said porous carrier.

13. The active compound of claim 12, wherein said at least one acid salt of an aminobenzene compound is supported on said solid porous carrier in an amount of 0.5 to 15 parts by weight to 100 parts by weight of said porous carrier.

14. The active compound of claim 1, wherein said at least one acid salt is an acid salt of p-chloroaniline.

15. The active compound of claim 1, wherein said at least one acid salt is an acid salt of ethyl p-aminobenzoate.

16. The active compound of claim 1, wherein said at least one acid salt is an acid salt of p-aminoacetanilide.

17. The active compound of claim 1, wherein said at least one acid salt is an acid salt of p-aminoacetophenone.

18. A material for removing offensive odors from an acetaldehyde-containing gas, consisting essentially of:

1) at least one acid salt of an aminobenzene compound having the formula:

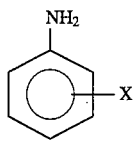

wherein X is halogen; —COOR, wherein R is an alkyl group; —SO$_2$NHR, wherein R is hydrogen, —NHCOCH$_3$ or —COCH$_3$; and 2) at least one additional material selected from the group consisting of transition metal compounds, iodine and iodines; and wherein said material is supported by a solid, inert, porous carrier.

* * * * *

UNITED STATES PATENT AND TRADEMARK OFFICE
CERTIFICATE OF CORRECTION

PATENT NO. : 5,603,927
DATED : February 18, 1997
INVENTOR(S) : Kazuhiro FUKUMOTO, et al.

It is certified that error appears in the above-identified patent and that said Letters Patent is hereby corrected as shown below:

Column 8, line 15, delete "an inert", and insert "a";
       line 40, delete "inert";
       line 43, after "zeolite" insert --activated carbon carbon fiber--;
       line 47, delete "inert".

Column 10, line 15, "iodines" should read --iodides--.

Signed and Sealed this

Seventh Day of April, 1998

Attest:

BRUCE LEHMAN

Attesting Officer      Commissioner of Patents and Trademarks